United States Patent [19]
Arevalos et al.

[11] Patent Number: 6,143,349
[45] Date of Patent: Nov. 7, 2000

[54] NO-HEAT JALAPEÑOS AND PRODUCTS COMPRISING NO-HEAT JALAPEÑOS

[75] Inventors: Don Arevalos; Lou Rasplicka, both of San Antonio, Tex.; Phil Villa, Camarillo, Calif.

[73] Assignee: Campbell Soup Company, Camden, N.J.

[21] Appl. No.: 09/316,214

[22] Filed: May 21, 1999

(Under 37 CFR 1.47)

Related U.S. Application Data

[62] Division of application No. 08/796,843, Feb. 6, 1997, Pat. No. 5,959,186.

[51] Int. Cl.[7] .............................. A01H 1/04; A23L 1/212
[52] U.S. Cl. ........................................ 426/615; 800/317.1
[58] Field of Search .......................... 800/317.1; 426/615

[56] References Cited

U.S. PATENT DOCUMENTS 5,066,830  11/1991  Morrison et al. ........................ 800/230
5,676,991  10/1997  Dull ........................................ 426/429

OTHER PUBLICATIONS

Levy et al., "Effect of genetic and environment factors on the capsaicin content in the fruits of pungent and sweet cultivars of pepper", *Capsicum anuumm*, L. Eucarpia VIIth meeting on genetics and breeding on capsicum and eggplant, Kragujevac, Yugoslavia, 1989.

Smith, et al., "Horticultural classification of peppers grown in the United States", *Hortscience*, vol. 22, No. 1, pp. 11–13, 1987.

Villanvon, "'Tam Mild Jalepeno–i' pepper", *Hortscience*, vol. 18, No. 3, pp.492–493, 1983.

Yazawa, et al., "Capsaicinoids content in the fruit of interspecific hybrids in Capsicum", *Journal of the Japanese Society of Horticultural Science*, vol. 58, No. 2, pp. 353–360; 1989.

Application for Plant Variety Protection Certificate, dated Feb. 7, 1996, Variety Name H78–1R.

Application for Plant Variety Protection Certificate, dated Feb. 7, 1996, Variety Name HM1–Y.

Application for Plant Variety Protection Certificate, dated Feb. 7, 1996, Variety Name V 10443.

*Primary Examiner*—Keith D. Hendricks
*Attorney, Agent, or Firm*—Baker Botts L.L.P.

[57] ABSTRACT

New, distinct and stable cultivars of no-heat Jalapeño peppers are disclosed. No-heat Jalapeño pepper cultivars are disclosed in which substantially all the pepper fruit produced comprise no capsaicin such as, capsaicin, dihydrocapsaicin, norhydrocapsaicin, homocapsaicin and homodihydrocapsaicin. The no-heat characteristic has been bred into 3 different cultivars of Jalapeño. This no-heat characteristic has been combined with many desirable Jalapeño traits including a lack of pungency, a dark green immature color, a saucer shaped calyx, a pendent fruit position, a rounded base shape, a blunt apex shape, a thick flesh thickness, an oblong shape, a concentrated fruit set, a long pedicel length, a straight pedicel shape, a slender pedicel thickness and a low capsaicinoid content. Methods for the reliable breeding to the no-heat Jalapeño characteristic into diverse Jalapeño peppers, as well as methods for production of food products comprising no-heat Jalapeños are disclosed.

9 Claims, 4 Drawing Sheets

NO-HEAT JALAPEÑOS AND PRODUCTS COMPRISING NO-HEAT JALAPEÑOS

This application is a divisional of Ser. No. 08/796,843, filed Feb. 6, 1997, now U.S. Pat. No. 5,959,186.

BACKGROUND

1. Field of the Invention

The present invention relates to new, distinct and stable cultivars of no-heat Jalapeños. No-heat Jalapeño pepper plants produce a pepper fruit which is absent of capsaicinoids such as capsaicin, dihydrocapsaicin, nordihydrocapsaicin, homocapsaicin and homodihydrocapsaicin. The no-heat Jalapeño fruit characteristic has been combined with many other known and desirable Jalapeño fruit characteristics including fruit shape, color, surface skin smoothness, flesh thickness and size.

The present invention also relates to methods for the breeding of no-heat fruit characteristics into Jalapeño cultivars. The present invention also relates to food products containing no-heat Jalapeños.

2. Description of the Related Art

Pepper and Pepper Flavor

The cultivated pepper, *Capsicum annuum*, is an important spice crop in the United States. There are many varieties of Capsicum, each adapted to produce a fruit for different purposes such as, for example, fresh consumption, dried spice or pickling. Varieties or cultivars of hot peppers are in everyday use include, for example, Anaheim, Ancho, Cascabel Cayenne, Charleston hot, Cherry, Chilaca, Chipotle, Fresno, Gaujillo, Habanera, Jalapeño, Pasilla and Pepperoncini. Of the many varieties or cultivars, Jalapeño is one of the most important and popular commercial peppers. Named after Jalapa, the capital of Veracruz, Mexico, Jalapeño peppers range from hot to very hot. Jalapeño peppers are consumed fresh, canned, and pickled. In addition, Jalapeños are used in a variety of sauces and in a multitude of cuisines.

The desirable qualities of a pepper are different depending upon the use and the individualized taste of each consumer. For some qualities of the fruit, such as heat, there is no consensus as to the proper amount. A Capsicum fruit that is too mild for one consumer may be extremely hot, unpalatable and irritating for another consumer.

The hot flavor of Capsicum is due to capsaicinoids, a family of chemical compounds. The flavors from capsaicinoids have been referred to by many terms, including heat, hotness, spiciness, pungency and chili (chile, chilli). Numerous terms such as sweet, no-heat, non-pungent and mild have also been used to describe low or undetectable levels of capsaicinoids. As a spice, capsaicinoids can produce a burning sensation in the mouth, causing the eyes to water, the nose to run, and in high amounts even induce perspiration. Capsaicinoids in peppers are produced in the cross wall placenta of a pepper fruit.

Because of the highly individualized, highly variable but narrow range between desirable taste and irritation for each individual, and because cultivated peppers are inconsistent in their capsaicinoid content, even from within the same field, it has been difficult to market food products comprising chili peppers with a uniform level of heat.

Analysis of Pepper Heat

The heat, or hot taste, in a Capsicum fruit has been established as a mixture of seven homologous branched chain alkyl vanillylamides named capsaicinoids. Capsaicin (C) (Merck Index, 11th edition, 1767), dihydrocapsaicin (DC), norhydrocapsaicin (NC), homocapsaicin (HC) and homodihydrocapsaicin (HDC) are the most prevalent and most important capsaicinoids for the hot flavor of peppers.

The hotness or heat of Capsicum fruit as a whole may be measured and compared by the Scoville heat test and expressed as Scoville heat unit. Even at dilutions of capsaicinoids down to 1 part in 16 million, a sensation of warmth may be detected by a human taster. The original Scoville heat test was an organoleptic test but Scoville heat units are now measured using high performance liquid chromatography determination of total capsaicinoids. Under the new test, total capsaicinoid content is measured in parts per million (ppm). One ppm is roughly equivalent to about 15 Scoville heat units. A hot pepper, such as habaneros, may have about 200,000 to about 300,000 Scoville heat units. Pure capsaicin has a Scoville heat unit score of about 16 million.

The amount of heat of a Capsicum fruit is affected both by genetic and environmental factors. Weather conditions, growing conditions and fruit age all contribute to the capsaicinoid content of a Capsicum fruit. Within a field and even within a fruit, the concentrations of capsaicinoids may be inconsistent. Known variables which affect heat content of Capsicum fruit include growth conditions such as moisture, temperature, light and fertilizer. Thus, it is difficult for providers of Capsicum fruit, and product comprising Capsicum fruit, to maintain product uniformity with regard to heat content. Neither cooking nor freezing diminishes capsaicin's intensity. The heat of Jalapeño peppers can only be reduced slightly by removal of the placenta from the fruit. While capsaicinoids may be removed from peppers through processes such as extraction, these processes are not economically feasible.

The inability to control the capsaicinoids (heat) content of peppers represents a major problem for food producers. At one concentration capsaicinoids are enjoyed as a spice, but at higher concentrations they are powerful irritants. The level differentiating spice from irritants is different for each individual. Further, many consumers cannot tolerate any capsaicinoids. Because of the variable heat content nature of peppers, and because of the variable consumer tolerance level for capsaicinoids, it is difficult to produce a food product with a uniform level of capsaicinoids without expensive and time consuming taste testing and HPLC or LC analysis.

SUMMARY OF THE INVENTION

The present invention overcomes the problems and disadvantages associated with current strategies and designs and provides methods for the production of no-heat Jalapeños.

An object of the invention is to provide Jalapeño cultivars having no heat.

Another object of the invention is to provide methods for the breeding of the no-heat Jalapeño characteristics into diverse Jalapeño cultivars.

An additional object of the invention is to provide methods and products comprising no-heat Jalapeño peppers.

These and other objects of this invention are met by one or more of the following embodiments.

In one embodiment, this invention provides a method for developing a no-heat Jalapeño pepper. In the method, a first pepper plant which produces a pepper fruit with undetectable levels of capsaicinoids, such as a sweet pepper, is crossed to a Jalapeño pepper plant which have detectable capsaicinoids. One or more selection and crossing step is performed until a pepper plant which produces pepper fruit with no detectable capsaicinoids is produced. The selection step comprises selecting for progeny plants which produces a progeny fruit with a reduced capsaicinoid content and Jalapeño characteristics. The crossing step comprises crossing the reduced capsaicinoid content progeny. The selection and crossing steps are preferably performed seven or more times. The Jalapeño characteristics used in the selection step may comprise: a lack of pungency, a dark green immature color, a saucer shaped calyx, a pendent fruit position, a rounded base shape, a blunt apex shape, a thick flesh thickness, an oblong shape, a concentrated fruit set, a long pedicel length, a straight pedicel shape and a slender pedicel thickness. The no-heat Jalapeño developed by the method preferably has a capsaicinoid content of less than about 0.5 parts per million. It is more preferable for the no-heat Jalapeño to have a capsaicinoid content less than about 0.1 parts per million capsaicinoids.

In another embodiment, this invention provides a no-heat Jalapeño pepper fruit comprising the qualities of: a lack of pungency, a dark green immature color, a saucer shaped calyx, a pendent fruit position, a rounded base shape, a blunt apex shape, a thick flesh thickness, an oblong shape, a concentrated fruit set, a long pedicel length, a straight pedicel shape, a slender pedicel thickness and a low capsaicinoid content. The Jalapeño pepper fruit may have a red mature color or a yellow mature color. The low capsaicinoid content is preferably less than 0.5 parts per million, more preferably less than 0.1 parts per million, and most preferably undetectable. Capsaicinoid as described herein includes may be capsaicin, dihydrocapsaicin, norhydrocapsaicin, homocapsaicin and homodihydrocapsaicin.

In yet another embodiment, this invention provides a no-heat Jalapeño fruit, or a part of the fruit, may be incorporated into food products. Food products may be, for example, fresh fruits, pickled fruits and sauces.

In still another embodiment of the invention is directed to a no-heat Jalapeño fruit producing plant, or a seed which when grown produces a no-heat Jalapeño fruit producing plant.

DESCRIPTION OF THE INVENTION

Figure 1:
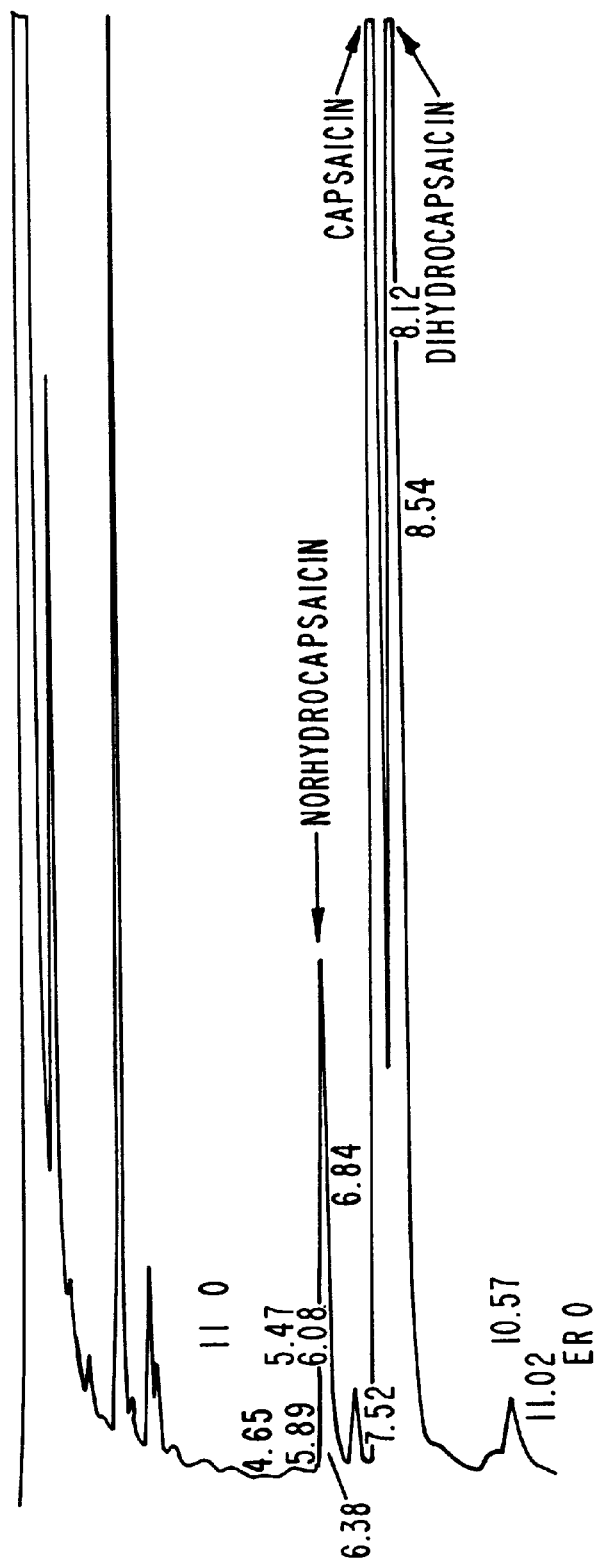
FIG. 1 depicts an HPLC analysis of a fruit of wild type Jalapeño.

As embodied and broadly described herein, the present invention is directed to a no-heat Jalapeño pepper cultivar, to methods of making a no-heat Jalapeño pepper cultivar, and to methods of making food products comprising a no-heat Jalapeño fruit, and to food products comprising a no-heat Jalapeño fruit.

Heat, also referred to as hotness, spicy, pungency, chili (chile, chilli), as used herein, refers to capsaicinoid content in the capsicum fruit.

As used herein, "no-heat" refers to lack of detectable capsaicinoid or less than 1 parts per million (ppm) capsaicinoid. No-heat has also been called sweet or non-pungent.

No-heat Jalapeño pepper cultivars according to this invention are stable, as evidenced by the stability of the trait through both asexual propagation and sexual crosses. Depending upon the cultivar, however, the plant size and the fruit size may be affected by environmental factors without any variance in the no-heat characteristic of the plant.

One embodiment of this invention was produced when parental strains C-023 sweet pepper and C-027 Jalapeño were crossed to produce the no-heat Jalapeño peppers. The plants are grown in standard agronomic conditions outdoors with temperatures above about 52° F.

Method of Crosses

Because pepper flowers are self pollinating, flowers of the plant to be used as female parent in a cross are typically emasculated to prevent self pollination. Emasculation comprises anther removal prior to pollination. The stigmatic surface is receptive for pollen following emasculation. Flowers to be used as the source of male parent pollen may be picked from the plant and used to pollinate from 3 to 5 flowers of the same cross combination. Pollen from the male parent is then applied to the stigmatic surface of the female parent. In this fashion, an abundance of pollen may be delivered to the stigmatic surface. Each pollinated flower should be marked to identify the date of pollination and the male and female parents.

Ripening of the fruit generally occurs at about 10 weeks after pollination, depending upon the environmental conditions. The collected seeds are typically cleaned by hand, and the seed separated from the fruit and stored in paper bags. Cool and cloudy weather increase the time required for ripening of the pepper fruit.

Flowers from peppers maintain functional male and female organs. Thus, incorporation of the no-heat fruit trait into a stable Jalapeño pepper cultivar has been possible. The no-heat characteristic, according to this invention, has been incorporated into multiple cultivars of Jalapeño with different Jalapeño genetic backgrounds and combined with a wide range of known and desirable Jalapeño characteristics.

Strategy of Crossing

A breeding program was undertaken, using sweet pepper and Jalapeño peppers as the starting parental strains, with the goal of selecting new and unique cultivars of Jalapeño peppers with having fruit characteristics, shown in Table 6, which are typical of Jalapeños but without the heat.

Typical Jalapeño characteristics are embodied in variety Jalapeño 'M', the standard by which all Jalapeños are judged. Jalapeño 'M' consists of upright plants approximately about 26 to about 30 inches in height. The fruit of Jalapeño 'M' matures dark green to red, with medium thick walls and a blunt-ended, sausage shape. Jalapeño 'M' produces uniform, medium-to-large size, pungent fruit for processing and fresh market uses. Selection criteria for typical Jalapeño 'M' characteristics are also listed in Tables 2 to 8.

Breeding of no-heat Jalapeño is initiated by crossing a sweet pepper breeding line with a breeding line having fruit characteristics of Jalapeños such as fruit shape, color, surface smoothness, flesh thickness, and size. Other suitable breeding lines include any elongated bell pepper and any large Jalapeños. Breeding of no-heat Jalapeños was accomplished by means of recurrent selection. Progeny with reduced heat as determined by taste and HPLC analysis, were selected and maintained in the breeding program.

In particular examples of this method, parental strains sweet pepper C-023 and Jalapeño C-027 were crossed and $F_1$ progeny were selected for Jalapeño fruit characteristics and low or no heat. (Desirable Jalapeño fruit characteristics are listed in Table 6.) The $F_1$ progeny were crossed to produce $F_2$, and the $F_2$ were selected under the same selection criteria used for F1. The selection process was continued until the 8th generation or $F_8$ which bore a large Jalapeño fruit that was free of capsaicinoids such as capsaicin, dihydrocapsaicin, norhydrocapsaicin, homocapsaicin and homodihydrocapsaicin. The best of Jalapeño plants, in terms of reduced heat and retention of Jalapeño characteristics, were selected. The seeds produced from these selections were sown. The resulting Jalapeño pepper plants showed reduced heat in successive selections and generations until finally plants were generated which comprise a pepper fruit comprising undetectable levels of capsaicinoids as determined by taste and HPLC analysis. In particular, H78-1R was selected from this breeding program for a red maturing fruit while HM1-Y was selected for a yellow maturing fruit.

As shown in the examples below, it is possible to breed and select for stable no-heat cultivars of Jalapeño or other peppers wherein substantially all the capsaicinoids (such as capsaicin, dihydrocapsaicin, norhydrocapsaicin, homocapsaicin and homodihydrocapsaicin) in the fruit are below detection levels. The no-heat characteristic also can be predictably bred into diverse peppers such as, for example, Jalapeños, Habanera, Tabasco, and Pequin. Alternatively, it is possible to cross the no-heat Jalapeño peppers with other hot Jalapeño peppers and select for low heat or no-heat progeny.

While three varieties of no-heat Jalapeños are specifically described herein, any pepper plant having a fruit with the characteristics of a Jalapeño but without capsaicin or a hot taste is within the contemplation of this invention. For example, Jalapeño varieties other than Varieties H78-1R, HM1-Y and V10443 may be bred with Varieties H78-1R, HM1-Y or V1044.3 as described herein to produce plants which yield no-heat pepper fruits. Appropriate parental strains to cross to arrive at the characteristics presently claimed will be readily apparent to those of ordinary skill in the art, in view of the present specification. Varieties of peppers with characteristics similar to the parental strains C-023 sweet pepper and C-027 Jalapeño are particularly suitable for use as parental strains. Any peppers within the same species are also suitable. It is within the contemplation of this invention to cross other pepper varieties with known varieties or varieties bred according to this invention in order to duplicate the invention. Such hybrids are intended to be covered by the present invention.

Any crosses between Varieties H78-1R, HM1-Y or V10443 will produce a pepper plant with Jalapeño fruit having the characteristics of the present inventions. Suitable combinations can be readily determined by those skilled in the art.

Applications for protection of Varieties H78-1R and HM1-Y under the Plant Variety protection Act have been filed with the U.S. Department of Agriculture, Plant Variety Protection Office on Feb. 13, 1996 and have been assigned PEPPER Application No. 9600138, 'H78-R.' and PEPPER Application No. 9600139, 'HM1-Y' respectively. An application for protection of Variety V10443 under the Plant Variety protection Act has been filed with the Department of Agriculture, Plant Variety Protection Office on Apr. 23, 1996 and has been assigned PEPPER Application No. 9600239, 'V10443' for Variety V10443. These cultivars are only examples of the lines of the present invention, and are not intended to be limiting to the scope of the present claims.

A detailed description of three no-heat Jalapeño peppers based on observations made from plants and fruits grown in a Mediterranean climate in Santa Paula, Calif. is as follows. Unless specified, the characteristics are the same for all three varieties. Other pepper plants and fruits with the same or similar characteristics are also within the contemplation of the invention.

The novel Varieties H78-1R, HM1-Y or V10443 are Jalapeño peppers of the Solanaceae family with the genus and species name of *Capsicum annuum*. H78-1 R requires about 90 days from transplant to develop a mature green color and about 105 days to develop a mature red color. From seeds, H78-1R requires about 110 days to mature green and about 170 days to develop a mature red fruit color. HM1-Y requires about 90 days from transplant to develop a mature green color and about 105 days to develop a mature red color. From seeds, HM1-Y requires about 115 days to mature green and about 170 days to develop a mature yellow fruit color. V10443 requires about 107 days from transplant to develop a mature green color and about 120 days to develop a mature red color. From seeds, HM1-Y requires about 128 days to mature green and about 141 days to develop a mature red fruit color. While both H78-1R and HM1-Y show a maturity from seed and maturity from transplants of about the same time as Jalapeños, variety V10443 mature from seed and transplants about 10 days earlier than Jalapeños.

With respect to the plant, H78-1R, HM1-Y and V10443 all have a compact habit with no basal branches and rigid branch flexibility when compared to Jalapeño 'M' plants. H78-1R stands about 51 cm high. Both H78-1R and HM1-Y have a width of about 61 cm which is about 10 cm narrower than Jalapeño 'M' plants grown in adjacent plots of land. V10443 is about 39 cm in width which is about 2 cm narrower than Jalapeño 'M'. H78-1R is about 51 cm high and about 24 cm shorter than Jalapeño 'M'. HM1-Y is about 61 cm high and about 14 cm shorter than Jalapeño 'M'. V10443 is about 39 cm high and 10 cm shorter than Jalapeño 'M'.

H78-1R, HM1-Y and V10443 all have dark green foliage with a lanceolate mature shape and a medium mature size which is comparable to the foliage of Anaheim Chili.

The flowers of H78-1R, HM1-Y and V10443 are similar with a calyx lobe number of about 6 and a petal number of about 6; white corolla, yellow (tan) corolla throat marking, style length less than stamen length, one flower per axil, no self incompatibility and no cytoplasmic male sterility.

With respect to the fruit, H78-1R, HM1-Y and V10443 all comprise fruits that have external appearance of Jalapeño 'M' with a saucer shaped calyx, oblong fruit shape, concentrated fruit set, straight pedicel shape. H78-1R, HM1-Y and V10443 share characteristics with Yolo Wonder L such as a lack of pungency, dark green immature color, smooth surface smoothness, a pendent fruit position and a blunt apex shape. H78-1R and V10443 have a red mature fruit color like Yolo Wonder L, while the color of the HM1-Y is lemon yellow. H78-1R and HM1-Y have thick flesh like Yolo Wonder L, while V10443 has medium flesh thickness more like Anaheim Chili. The fruits of all three varieties have the slender pedicel thickness like a Cayenne pepper and a long pedicel length like an Anaheim Chili. The fruits of H78-1R are larger with a length of about 12 cm, which is about 3 cm longer than Jalapeño 'M'. Each H78-1R fruit weights on average about 80 grams with a diameter of about 40 mm at calyx attachment. The number of locules of H78-1R varies between about 3 to about 4. The fruits of HM1-Y are also larger with a length of about 13 cm, which is about 4 cm longer than Jalapeño 'M'. Each HM1-Y fruit weights on average of about 80 grams with a diameter of about 3 cm at calyx attachment. The number of locules of HM1-Y varies between about 3 to about 4. The fruits of V10443 are smaller with a length of about 5 cm, which is about 2 cm longer than Jalapeño 'M'. Each H78-1R fruit weights on average of about 9 grams with a diameter of about 23 mm at calyx attachment. The number of locules of H78-1R varies between about 2 to about 3.

The seeds of Variety H78-1R, HM1-Y and V10443 are all yellow. Variety H78-1R seeds weight 8 g per 1000 seeds. Variety HM1-Y weights 9 grams per 1000 seeds and Variety V10443 weights 5 grams per 1000 seeds.

The characteristics of H78-1R, HM1-Y and V10443 with respect to anthocyanin are similar. It is present in stem and node but absent in the leaf, calyx, pedicel, seedling hypocotyl and fruit of the plant.

In summary, H78-1R, HM1-Y and V10443 most resemble Jalapeño 'M' in maturity, plant habit, leaf color, leaf shape, fruit shape, and immature fruit color. H78-1R, HM1-Y and V10443 most resemble Yolo Wonder L in pungency. While H78-1R and V10443 most resemble Jalapeño 'M' in mature fruit color, V10443 most resembles Golden Bell in mature fruit color.

Other embodiments and advantages of the invention are set forth, in part, in the description which follows and, in part, will be obvious from this description and may be learned from practice of the invention.

EXAMPLES

Example 1
Selection of New No-Heat Jalapeño Cultivars by Means of Crossing a C-023 Sweet Pepper Cultivar to a C-027 Jalapeño Cultivar.

New no-heat Jalapeño breeding lines were produced by means of crossing a selected C-023 Sweet pepper breeding line to a C-027 Jalapeño breeding line. Sweet Pepper cultivar C-023 was crossed as the female parent to the Jalapeño pepper cultivar C-027 as the male parent. A detailed description of the resulting progeny is contained in Table I. The detailed description is based on plants produced in a Mediterranean climate in Santa Paula, Calif. during the winter season. Plants were grown outdoors under standard agricultural conditions for peppers. Height measurements were taken from the soil line. The phenotype of all progeny produced from the following crosses were ascertained under the same environmental conditions and using the same methods.

TABLE 1

Genus and Species

| Variety Name | H78-1R | HM1-Y | V10443 |
| --- | --- | --- | --- |
| Genus and Species | Capsicum annuum | Capsicum annuum | Capsicum annuum |
| Family | Solanaceae | Solanaceae | Solanaceae |
| Crop or Common Name | Jalapeño | Jalapeño | Jalapeño |

TABLE 2

Market Maturity

| Variety Name | H78-1R | HM1-Y | V10443 |
| --- | --- | --- | --- |
| Days from transplant to mature green | 90 | 90 | 107 |

TABLE 2-continued

Market Maturity

| Variety Name | H78-1R | HM1-Y | V10443 |
| --- | --- | --- | --- |
| Days from transplant to mature red or yellow | 105 | 105 | 120 |
| Days from seed to mature green | 110 | 115 | 128 |
| Days from seed to mature red or yellow | 170 | 170 | 141 |
| Maturity days from transplant | Same as Jalapeño | Same as Jalapeño | 10 days earlier than Jalapeño |
| Maturity days from seed | Same as Jalapeño | Same as Jalapeño | 10 days earlier than Jalapeño |

TABLE 3

Plant Characteristics

| Variety Name | H78-1R | HM1-Y | V10443 |
| --- | --- | --- | --- |
| Habit | Compact | Compact | Compact |
| Height | 51 | 61 cm | 39 |
| Height compared to Jalapeño | 24 cm shorter | 14 cm shorter | 10 cm shorter |
| Width | 61 cm | 61 cm | 39 cm |
| Width compared to Jalapeño | 10 cm narrower | 10 cm narrower | −2 cm narrower |
| Length of 3rd internode | 28 mm | 30 mm | 80 mm |
| Basal branches | none | none | none |
| Branch flexibility | Rigid | Rigid | Rigid |

TABLE 4

Leaf Phenotype

| Variety Name | H78-1R | HM1-Y | V10443 |
| --- | --- | --- | --- |
| Foliage color | Dark Green | Dark Green | Dark Green |
| Mature Shape | Lanceolate | Lanceolate | Lanceolate |
| Mature Size | Medium (Anaheim Chili) | Medium (Anaheim Chili) | Medium (Anaheim Chili) |

TABLE 5

Flower Phenotype

| Variety Name | H78-1R | HM1-Y | V10443 |
| --- | --- | --- | --- |
| Calyx lobe number | 6 | 6 | 6 |
| Petal number | 6 | 6 | 6 |
| Corolla Color | White | White | White |
| Corolla throat marking color | Yellow (tan) | Yellow (tan) | Yellow (tan) |
| Another color | Yellow | Yellow | Yellow |
| Style length | Less than stamen | Less than stamen | Same as stamen |
| Flower per leaf axil | 1 | 1 | 1 |
| Self incompatibility | Absent | Absent | Absent |
| Cytoplasmic Male Sterility | Absent | Absent | Absent |

TABLE 6

Fruit Phenotype

| Variety Name | H78-1R | HM1-Y | V10443 |
| --- | --- | --- | --- |
| Group | Jalapeño | Jalapeño | Jalapeño |
| Pungency | Sweet (Yolo Wonder L) | Sweet (Yolo Wonder L) | Sweet (Yolo Wonder L) |

TABLE 6-continued

Fruit Phenotype

| Variety Name | H78-1R | HM1-Y | V10443 |
|---|---|---|---|
| Immature color | Dark Green (Yolo Wonder L) | Dark Green (Yolo Wonder L) | Dark Green (Yolo Wonder L) |
| Mature color | Red (Yolo Wonder L) | Lemon Yellow | Red (Yolo Wonder L) |
| Surface smoothness | Smooth (Yolo Wonder L) | Smooth (Yolo Wonder L) | Smooth (Yolo Wonder L) |
| Calyx shape | Saucer shaped | Saucer shaped | Saucer shaped |
| Position | Pendent (Jalapeño) | Pendent (Jalapeño) | Pendent (Jalapeño) |
| Base shape | Rounded (Jalapeño) | Rounded (Jalapeño) | Rounded (Jalapeño) |
| Apex shape | Blunt (Yolo Wonder L) | Blunt (Yolo Wonder L) | Blunt (Yolo Wonder L) |
| Flesh thickness | Thick (Yolo Wonder L) | Thick (Yolo Wonder L) | Medium (Anaheim Chili) |
| Length | 12 cm | 13 cm | 5 cm |
| Compared to Jalapeño | 3 cm longer | 4 cm longer | 2 cm shorter |
| Diameter at calyx attachment | 40 mm | 32 mm | 23 |
| Weight per fruit | 79.7 grams | 78 grams | 9 grams |
| Fruit Shape | Oblong (Jalapeño) | Oblong (Jalapeño) | Oblong (Jalapeño) |
| Fruit Set | Concentrated | Concentrated | Concentrated |
| Number of Locules | 3 to 4 | 3 to 4 | 2 to 3 |
| Pedicel Length | Long (Anaheim Chili) | Long (Anaheim Chili) | Long (Anaheim Chili) |
| Pedicel Shape | Straight | Straight | Straight |
| Pedicel Thickness | Slender (Cayenne) | Slender (Cayenne) | Slender (Cayenne) |

\* Characteristic is described by comparison with a known variety having similar characteristic.

TABLE 7

Seed Phenotype

| Variety Name | H78-1R | HM1-Y | V10443 |
|---|---|---|---|
| Color | Yellow | Yellow | Yellow |
| Weight | 8 g per 1000 seed | 9 g per 1000 seed | 5 g per 1000 seed |

TABLE 8

Anthocyanin

| Variety Name | H78-1R | HM1-Y | V10443 |
|---|---|---|---|
| Leaf | Absent | Absent | Absent |
| Stem | Present | Present | Absent |
| Node | Present | Present | Present |
| Calyx | Absent | Absent | Absent |
| Pedicel | Absent | Absent | Absent |
| Seedling Hypocotyl | Absent | Absent | Absent |
| Fruit | Absent | Absent | Absent |
| Disease Reaction | Not Tested | Not Tested | Not Tested |

TABLE 9

Variety Most Closely Resemble

| Variety Name | H75-1R | HM1-Y | V10443 |
|---|---|---|---|
| Maturity | Jalapeño 'M' | Jalapeño 'M' | Jalapeño 'M' |
| Plant habit | Jalapeño 'M' | Jalapeño 'M' | Jalapeño 'M' |
| Leaf color | Jalapeño 'M' | Jalapeño 'M' | Jalapeño 'M' |
| Leaf shape | Jalapeño 'M' | Jalapeño 'M' | Jalapeño 'M' |
| Fruit shape | Jalapeño 'M' | Jalapeño 'M' | Jalapeño 'M' |
| Immature fruit color | Jalapeño 'M' | Jalapeño 'M' | Jalapeño 'M' |
| Mature fruit color | Jalapeño 'M' | Jalapeño 'M' | Jalapeño 'M' |
| Pungency | Yolo Wonder L | Yolo Wonder L | Yolo Wonder L |

Example 2
HPLC Analysis of No-Heat Jalapeño Extraction

Fresh samples of capsicum fruits such as no-heat Jalapeño may be sun dried or freeze dried and ground into capsicum powder for subsequent analysis. About 25 grams of dehydrated or fresh ground capsicum fruit is placed into a 500 ml flask. 200 ml ethanol and several glass beads are added to the flask. The 500 ml flask is attached to a reflux condenser. The contents are gently refluxed for 5 hours and then allowed to cool. About 1 to 4 ml of the cooled solution is cleaned by passage through a 0.45 micron syringe filter and stored into small glass vials as samples for liquid chromatography analysis. For low capsaicinoid content peppers, a more sensitive assay was performed by using more capsicum fruits in the same volume of ethanol and adjusting the results accordingly. For example, the heat content should be divided by 2 when twice as much starting material is extracted in the same volume of ethanol.

Standard capsaicin solutions were prepared using N-vanillyl-n-nonanamide, a synthetic analog of capsaicin. A 0.015 mg/ml solution of N-vanillyl-n-nonanamide (Penta international Corp, Livingston, N.J.) is prepared by dissolving 15 mg of N-vanillyl-n-nonanamide (Penta international Corp, Livingston, N.J.) in 1 L ethanol (95% grade or better, Sigma, St Louis, Mo.).

The extracted capsaicinoids and the standard solutions were analyzed by a high performance liquid chromatograph with a 1 V integrator, 20 µl sample injector, with an UV detector set at 280 nm wavelength or fluorometer with excitation 280 nm and emission 325 nm. Chromatography was performed in an ambient temperature, about 20° C. to about 25° C., under isocratic conditions. A stainless steel $C_{18}$ column, 150 mm long with a 4.6 mm inner diameter, with a 5 micron particle size was used for chromatographic separation. Flow rate was set at 1.5 ml per minute. Under these conditions, the relative retention times are: N-vanillyl-n-nonanamide, 1.00; nordihydrocapsaicin, 0.90; capsaicin, 1.00; dihydrocapsaicin, 1.58.

Analysis is begun with an injection of 20 µl of standard N-vanillyl-n-nonanamide solution into the HPLC apparatus. Up to 6 samples may be injected and tested following standard solution injection. The standard solution is reinjected at intervals of 6 samples or less. After every 30 sample injections or less, the HPLC column is purged for 30 minutes with 100% acetonitrile at 1.5 ml per minute flow rate.

Capsaicinoid concentration is calculated as follows:
For UV detection $N=(P_N/P_S) \times (C_S/W_T) \times (200/0.98) \times 9300$
$C=(P_C/P_S) \times (C_S/W_T) \times (200/0.89) \times 16100$
$D=(P_D/P_S) \times (C_S/W_T) \times (200/0.93) \times 16100$ For Fluorescence detection:

$N=(P_N/P_S) \times (C_S/W_T) \times (200/0.92) \cdot 9300$ $C=(P_C/P_S)\times(C_S/W_T)\times(200/0.88)\cdot 16100$ $D=(P_D/P_S)\times(C_S/W_T)\times(200/0.93)\cdot 16100$ Total capsaicinoid in SHU=N+C+D ppm capsaicin×15=Scoville units (assumes capsaicin=15,000,000 Scoville)

N=nordihydrocapsaicin concentration in Scoville Heat Units (SHU)

C=capsaicin concentration in Scoville Heat Units (SHU)

D=dihydrocapsaicin concentration in Scoville Heat Units (SHU)

Figure 2:
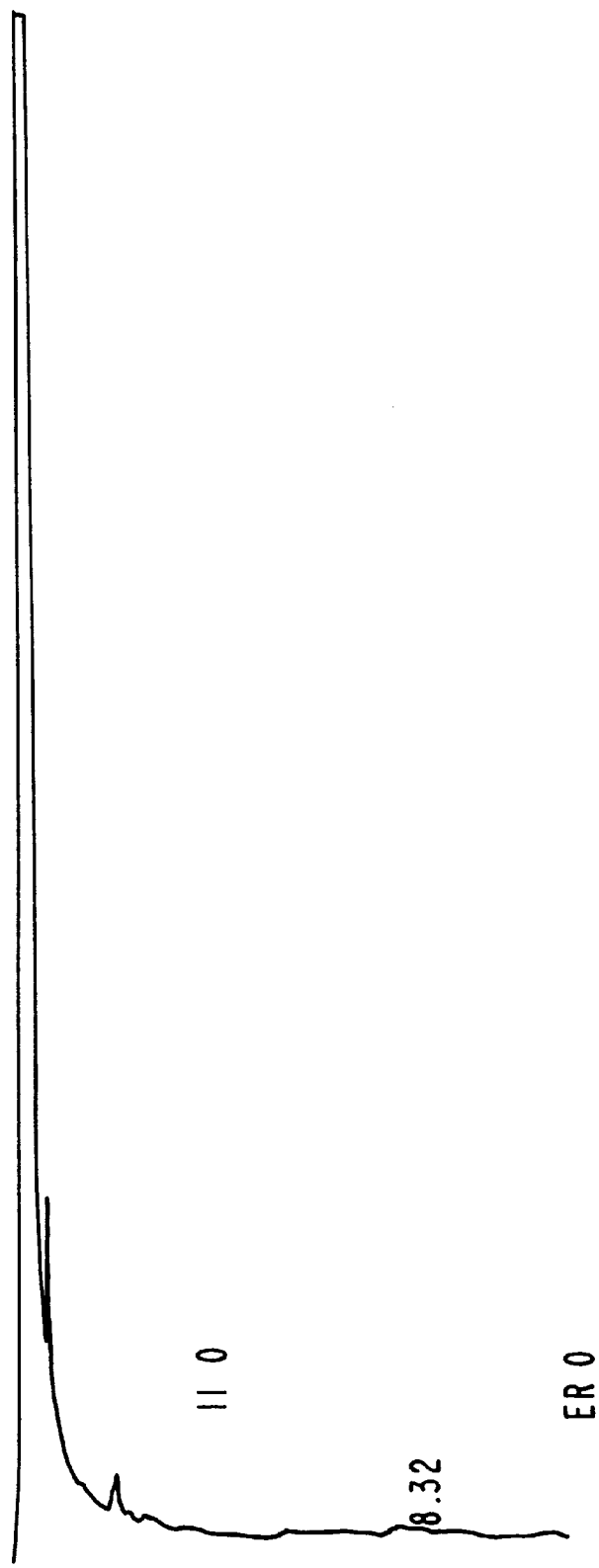
FIG. 2 depicts an HPLC analysis of a fruit of no-heat Jalapeño Pepper cultivar H78-1R.
Figure 3:
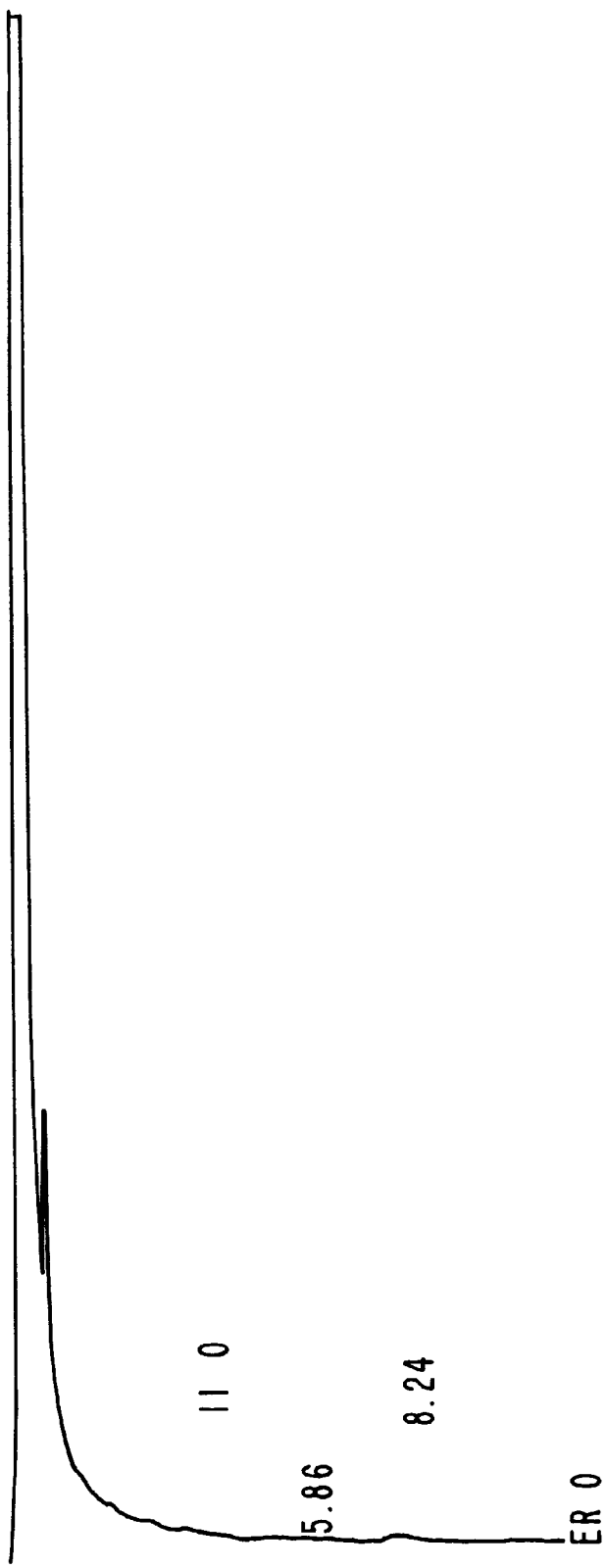
FIG. 3 depicts an HPLC analysis of a fruit of no-heat Jalapeño Pepper cultivar HM1-Y.
Figure 4:
FIG. 4 depicts an HPLC analysis of a fruit of no-heat Jalapeño Pepper cultivar V10443.

$P_N$=average peak area for nordihydrocapsaicin from multiple analysis $P_C$=average peak area for capsaicin from multiple analysis $P_D$=average peak area for dihydrocapsaicin from multiple analysis $C_S$=concentration of standard solution in mg/ml $W_T$=weight of test sample in grams Analysis of Jalapeño 'M' pepper indicates detectable levels of capsaicinoids (FIG. 1). Analysis of No-heat Jalapeño H78-1R (FIG. 2), HM1-Y (FIG. 3) and V10443 (FIG. 4) show no detectable levels of capsaicinoids. Thus, the heat content of Jalapeño H78-1R, HM1-Y and V10443 is below detectable limits.

Example 3
Stability and Quantitative Analysis of the No-Heat Trait

The stability of the no-heat Jalapeño pepper and subjective and quantitative analysis of capsicum expression in Jalapeño pepper fruit was analyzed. Crosses were made between no-heat Jalapeño peppers and seeds from the crosses were sown and F1 fruit and seeds were collected. In order to ascertain the stability of the no-heat phenotype, the capsicum expression in the fruit was compared to control parental strains both by subjective testing and by HPLC testing. The seeds were transplanted and the plants allowed to bear fruit. Six different progenies, resulting from crosses between H78-1R and H78-1R, between HM1-Y and HM1-Y, between V10443 and V10443, between H78-1R and HM1-Y, between HM1-Y and V10443, and between V10443 and H78-1R were analyzed for capsaicinoid level. Progeny from all six crosses showed undetectable capsaicinoid level.

The absence of expression of capsaicin was repeated in all three crossings taken from each of the three strains. The level of expression of capsaicin was consistently below detectable limits.

Example 4
Recipe for Production of Extra Mild Salsa Using No-heat Jalapeño

Combine about 250 grams of fresh diced tomatoes, about 250 grams of fresh diced onions, about 235 grams of water, about 200 grams of fresh diced No-Heat Jalapeños, about 25 grams of vinegar, about 20 grams of salt and about 20 grams of fresh minced garlic. Very ripe tomatoes and white onions are preferred for use in this recipe.

The salsa sauce may be used fresh or may be refrigerated, for up to seven days, for subsequent use. If salsa is to be kept for a long period of time, it may be canned or preserved using techniques known to those of skill in the art of canning and preservation.

Other embodiments and uses of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

We claim:

1. A food product comprising at least a portion of a Jalapeño pepper fruit, wherein said pepper fruit comprises the following qualities:
   a) a capsaicinoid content of less than 1 part per million;
   b) a dark green immature color;
   c) a saucer shaped calyx;
   d) a pendent fruit position;
   e) a rounded base shape;
   f) a blunt apex shape;
   g) a thick flesh thickness;
   h) an oblong shape;
   i) a long pedicel length;
   j) a straight pedicel shape; and
   k) a slender pedicel thickness.

2. The food product of claim 1 selected from the group consisting of fresh fruits, pickled fruits and sauces.

3. The food product of claim 1, wherein said pepper fruit has a red mature color.

4. The food product of claim 1, wherein said pepper fruit has a yellow mature color.

5. The food product of claim 1, wherein said pepper fruit contains no detectable amount of capsaicin, dihydrocapsaicin, norhydrocapsaicin, homocapsaicin or homodihydrocapsaicin.

6. The food product of claim 1, wherein said capsaicinoid content is less than 0.5 parts per million.

7. The food product of claim 1, wherein said capsaicinoid content is less than 0.1 parts per million.

8. The food product of claim 1, wherein said capsaicinoid content is undetectable.

9. A method for preparing a salsa comprising
   (A) dicing a Jalapeño pepper fruit, wherein said pepper fruit comprises the following qualities:
      a) a capsaicinoid content of less than 1 part per million;
      b) a dark green immature color;
      c) a saucer shaped calyx;
      d) a pendent fruit position;
      e) a rounded base shape;
      f) a blunt apex shape;
      g) a thick flesh thickness;
      h) an oblong shape;
      i) a long pedicel length;
      j) a straight pedicel shape; and
      k) a slender pedicel thickness, and
   (B) incorporating the diced pepper fruit into a food product, wherein the food product is a salsa.

* * * * *